(12) United States Patent
Grasse et al.

(10) Patent No.: US 10,576,284 B2
(45) Date of Patent: Mar. 3, 2020

(54) SYSTEMS AND METHODS FOR SWITCHED ELECTRODE STIMULATION FOR LOW POWER BIOELECTRONICS

(71) Applicant: The Board of Regents of The University of Texas System, Austin, TX (US)

(72) Inventors: Dane W Grasse, Richardson, TX (US); Robert L Rennaker, II, Sachse, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 221 days.

(21) Appl. No.: 15/590,590

(22) Filed: May 9, 2017

(65) Prior Publication Data
US 2017/0326370 A1    Nov. 16, 2017

Related U.S. Application Data

(60) Provisional application No. 62/333,921, filed on May 10, 2016.

(51) Int. Cl.
| | |
|---|---|
| *A61N 1/00* | (2006.01) |
| *A61N 1/36* | (2006.01) |
| *A61N 1/06* | (2006.01) |
| *A61N 1/08* | (2006.01) |
| *H01H 3/02* | (2006.01) |
| *A61N 1/378* | (2006.01) |

(52) U.S. Cl.
CPC .......... *A61N 1/36103* (2013.01); *A61N 1/06* (2013.01); *A61N 1/08* (2013.01); *A61N 1/36125* (2013.01); *A61N 1/36171* (2013.01); *A61N 1/3787* (2013.01); *H01H 3/02* (2013.01)

(58) Field of Classification Search
CPC ............. A61N 1/36103; A61N 1/3605; A61N 1/36062; A61N 1/3787; A61N 1/36171; A61N 1/36125; A61N 1/08; A61N 1/06; H01H 3/02
See application file for complete search history.

(56) References Cited

U.S. PATENT DOCUMENTS

| | | | |
|---|---|---|---|
| 7,630,771 B2 | 12/2009 | Cauller | |
| 8,457,757 B2 | 6/2013 | Cauller | |
| 8,958,968 B2 | 2/2015 | Ghovanloo | |
| 2010/0106041 A1 | 4/2010 | Ghovanloo | |
| 2014/0094674 A1 | 4/2014 | Nurmikko et al. | |
| 2016/0367159 A1* | 12/2016 | Fisk | H01L 21/042 |
| 2017/0100595 A1* | 4/2017 | Persson | A61N 1/371 |

OTHER PUBLICATIONS

Catrysse et al. "An inductive power system with integrated bi-directional data-transmission." *Sensors and Actuators A: Physical* 115.2 (2004): 221-229.

(Continued)

*Primary Examiner* — Scott M. Getzow
(74) *Attorney, Agent, or Firm* — Parker Highlander PLLC

(57) ABSTRACT

Systems and methods for stimulating tissue. Exemplary embodiments include systems and methods configured to maintain one electrode at a fixed voltage potential and switching a second electrode between different fixed voltage potentials.

17 Claims, 5 Drawing Sheets

(56) References Cited

OTHER PUBLICATIONS

Chun et al., "Implantable stimulator for bipolar stimulation without charge balancing circuits," in *Biomedical Circuits and Systems Conference (BioCAS), 2010 IEEE,* 2010, pp. 202-205.

Harrison et al., "A low-power integrated circuit for a wireless 100-electrode neural recording system," *IEEE J. Solid-State Circuits,* vol. 42, No. 1, pp. 123-133, 2007.

Lee et al., "An inductively powered scalable 32-channel wireless neural recording system-on-a-chip for neuroscience applications," *IEEE Trans. Biomed. Circuits Syst.,* vol. 4, No. 6, pp. 360-371, 2010.

Rosellini et al. "A Voltage-Controlled Capacitive Discharge Method for Electrical Activation of Peripheral Nerves." *Neuromodulation: Technology at the Neural Interface* 14.6 (2011): 493-500.

Simpson and Ghovanloo, "An experimental study of voltage, current, and charge controlled stimulation front-end circuitry." *Circuits and Systems, 2007. ISCAS 2007. IEEE international Symposium on.* IEEE. 2007.

Sodagar et al., "A wireless implantable microsystem for multichannel neural recording," *IEEE Trans. Microw. Theory Tech.,* vol. 57, No. 10, pp. 2565-2573, 2009.

Vidal and Ghovanloo. "Towards a switched-capacitor based stimulator for efficient deep-brain stimulation." *Engineering in Medicine and Biology Society (EMBC), 2010 Annual International Conference of the IEEE.* IEEE, 2010.

\* cited by examiner

SYSTEMS AND METHODS FOR SWITCHED ELECTRODE STIMULATION FOR LOW POWER BIOELECTRONICS

CROSS-REFERENCE TO RELATED APPLICATIONS

This application claims priority to U.S. Provisional Patent Application Ser. No. 62/333,921 filed May 10, 2016, the entire contents of which are incorporated by reference herein.

BACKGROUND INFORMATION

Existing systems for tissue stimulation include implants that are powered by complex circuitry and control systems. Typical systems include an external battery powered transreceiver that inductively couples power/control signals to an implanted coil, thereby powering the implanted device (electronics) and providing stimulus current for the electrodes. The inductive coupling is generally bi-directional i.e. power and data flow from external transreceiver to the implanted device and modulated data from the implanted device to the external transreceiver thereby enabling stimulation and recording. In addition, existing systems typically provide stimulation via electrodes continuously coupled to a variable voltage source.

As discussed in further detail below, exemplary embodiments of the present disclosure address shortcomings of existing systems and provide notable benefits in comparison to such systems.

SUMMARY

Exemplary embodiments of the present disclosure comprise systems and methods for switching electrodes between different electrical potentials to stimulate tissue, including for example nerve tissue. Specific embodiments comprise systems and methods of delivering short duration (e.g. 5 µs) current pulses into tissue at rates as fast as 200,000 times per second. Particular embodiments accomplish this by holding one electrode at a fixed voltage potential and rapidly switching a second electrode between different fixed voltage potentials. As explained in further detail below, exemplary embodiments effectively use the electrode double layer capacitance to sink or source current to the tissue, and do not require amplifiers to generate current waveforms. In addition, the current amplitude of the pulses is largely independent of electrode impedance and surface area. Exemplary embodiments are effective at activating nerves with lower voltage, charge, and power requirements as compared to conventional controlled-current stimulation.

In particular embodiments, two electrodes begin at the same potential (typically designated as 0 V) and one electrode is switched to a different potential (e.g., 1 V). After the voltage switch is made to one electrode, current begins to flow from the electrode through tissue. The current decreases exponentially with time due to the charging of the electrode double layer capacitance between the electrode and the tissue. Once the electrode double layer capacitance has been charged, the electrodes are switched back to the same potential. Current is then discharged out of the electrodes, decreasing exponentially over time.

Accordingly, exemplary embodiments utilize voltage controlled stimulation that operate by varying the voltage applied to the electrodes. Unlike typical voltage controlled stimulation systems and methods, however, exemplary embodiments switch the electrodes to a fixed voltage source, rather than being continuously connected to a variable voltage source.

Exemplary embodiments also differ from current-controlled stimulation systems and methods, which are more common in nerve stimulation than voltage controlled stimulation examples. For example, current-controlled methods require amplifiers to vary the voltage in a feedback manner so that a specified current is achieved. Exemplary embodiments, however do not require amplifiers and active feedback, and therefore can use much less power than current-controlled methods, since amplifiers dissipate power constantly, unlike a voltage source. Exemplary embodiments also require fewer components than current-controlled methods, potentially increasing reliability and reducing costs.

Exemplary embodiments provide other potential benefits as well. For example, current waveforms (i.e. the current profile over time) generated by exemplary methods and systems have physiological advantages over other techniques. Experimental data shows that nerves become activated using significantly less overall charge compared to a square current pulse produced by other existing systems. It is possible this results from the high peak currents generated at the time of the voltage switch to the electrode.

In certain embodiments, switched electrode stimulation may include additional modifications and components. For example, a direct current (DC) blocking capacitor can be added in series with the electrodes. This can prevent potentially harmful DC current from flowing through tissue. In addition, a sense resistor can be added in series with the electrodes, which can allow monitoring of stimulation current. In particular embodiments, both electrodes can be switched instead of just one. This can allow for symmetrical charging and discharging of the electrodes so that net charge on electrodes is zero over time.

Exemplary embodiments can also include an implanted device that is a passive stimulator (e.g. it is only powered in the presence of a magnetic field). For example, an alternating magnetic field generated outside the body can cause the implanted device to turn on and begin stimulating nervous tissue through the electrodes. The stimulation parameters (amplitude, frequency, pulse duration) can either be hard-programmed into the device or controllable through modulation of the magnetic field. During operation, the stimulation stops when the magnetic field turns off. Exemplary embodiments can utilize a stimulation method that injects current into the electrode by switching either end to a fixed potential and allowing the electrode capacitance to sink/source current, referred to herein as Switched Electrode Stimulation (SES).

In certain embodiments, the magnetic field induces an alternating current (AC) voltage on the attached coil of the implanted device. This AC voltage can then be rectified and smoothed to produce DC voltage. In particular embodiments, the DC voltage is limited by a Zener diode and regulated to a specified amplitude using a linear regulator. The regulator provides power to the rest of the integrated circuits on the implanted device, and also feeds a resistor capacitor (RC) timer.

In particular embodiments, the RC timer is composed of a Schmitt trigger with a capacitor going from the input to ground. During operation, the regulator charges this input capacitor through a resistor, and when a positive-going threshold voltage is reached the Schmitt trigger output changes from low to high. This change turns on a switch, which discharges the input capacitor through a second resistor. Once the input capacitor reaches the negative going threshold, the Schmitt trigger output changes from high to low, which turns the switch off and again begins the charging of the input capacitor. By selecting the values of the charging resistor and the discharging resistor, the pulse frequency and pulse duration of the RC timer can be hard-programmed into the device.

During operation, the output of the RC timer is fed to a data (D) flip-flop configured as a frequency divider. This frequency divider outputs a high or low level that alternates with each pulse. The frequency divider controls a single pole double throw (SPDT) switch, which sends the RC timer output to one of two channels alternatively. In certain embodiments, each of the two channels of this SPDT switch is connected to the control pin of a separate SPDT switch (3 SPDT switches in total). The two additional SPDT switches have their common pins connected to either end of the electrode, and the remaining two pins on each of the additional SPDT switches are connected to ground and to a positive voltage that is the stimulation amplitude. During a single cycle of stimulation one end of the electrode is switched from ground to positive voltage and back to ground again, while the other end is held at ground. In the next cycle of stimulation, the second end of the electrode is switched to the positive voltage while the first end is held at ground. During normal operation, the two ends of the electrode take turns receiving a positive pulse.

When one end of the electrode is switched from ground to a positive voltage, current flows into the electrode to charge the electrode-electrolyte capacitance. After the electrode has partially charged, the same end is switched back to ground which causes current to flow out of the electrode, discharging it. The current pulses produced after each switching event have an exponentially decaying waveform shape. Since the charge leaves the electrode passively, it may not completely discharge by the next stimulation pulse. Therefore to prevent charge buildup over multiple stimulation cycles, the end of the electrode which receives the positive voltage pulse can be alternated for each stimulation cycle. A DC blocking capacitor can also be placed in series with the electrode to prevent DC current flow.

In exemplary embodiments, the stimulation amplitude can be hard-programmed into the device by using a normal resistive divider from the regulator output. The stimulation amplitude can also be controlled remotely by the use of a frequency-controlled voltage (FCV) circuit included in the implanted device. During operation, the FCV circuit takes the voltage from the implanted coil and feeds it through a resistor-inductor-capacitor (RLC) voltage divider. The RLC voltage divider consists of a resistor in series with a parallel inductor-capacitor (LC) tank. The impedance of the LC tank changes based on the magnetic field frequency, which in turn changes the impedance ratio between the resistor and the LC tank. Since the implanted coil voltage is limited by a Zener diode, the voltage sent to the RLC divider is a fixed (provided the minimum field strength is supplied). This allows precise control of the RLC divider output voltage based on frequency.

As disclosed herein, switched electrode stimulation (SES) is a novel stimulation technique that delivers current to the nerve with a greatly reduced circuit complexity (e.g. with fewer and smaller components than existing systems). SES also requires lower supply voltages than traditional controlled current stimulation methods. Unlike typical existing systems, SES does not require any onboard capacitor to be charged or discharged during stimulation, allowing for higher frequencies and reduced circuit complexity.

The method by which SES performs "charge balancing" with the positive and negative stimulation pulses is also an improvement over typical existing systems. Most stimulators are either actively charge balanced (requiring feedback amplifiers) or passively charge balanced (which creates a DC potential on the electrodes over time). Although each pair of positive/negative pulses is passively charge balanced in SES, alternating the end of the electrode that receives the pulses eliminates any DC potential from forming over time.

The method to control stimulation amplitude remotely through the Frequency Controlled Voltage (FCV) circuit is also an improvement over existing systems. The use of the RLC voltage divider in the FCV circuit to control stimulation amplitude remotely is also an improvement over existing systems. This method is significant because it is a straightforward way to control stimulation amplitude while being independent of the field strength. The stimulation amplitude should not be controlled by (or depend on) the external field strength because small motions between the external coil and the implanted coil will cause undesirable, unpredictable changes to the stimulation amplitude. Amplitude or frequency modulated communication is effective, but requires active components for demodulating the signal, which take up space and power. The FCV method is precise, independent of coil positions or field strength, and uses only 3 to 5 discrete passive components to accomplish the task.

The method of using a compound nerve action potential to send a backscattered pulse to the external coil is also an improvement over existing systems. Recording biopotential signals with an implanted device and transmitting them out of the body in general is known, but exemplary embodiments accomplish this with minimal circuitry. Taking advantage of the discrete nature of an action potential, exemplary embodiments can encode this event using discrete communication (a single pulse). Using only an amplifier and a MOSFET, an analog threshold is applied to the nerve signal which modulates the impedance of the implanted coil. This impedance change can be detected by the external coil. Existing systems do not communicate the occurrence of a nerve action potential with such minimal electronics as those used in exemplary embodiments.

Exemplary embodiments include a system for stimulating tissue, the system comprising: a fixed voltage source; a first electrode; a second electrode; and a switch coupled to the first electrode. In certain embodiments the first electrode and the second electrode are initially at a first voltage potential; the fixed voltage source is at a second voltage potential; and the switch is configured to alternately couple and de-couple the first electrode to the fixed voltage source. In particular embodiments, an electrical double layer between the tissue and the first and second electrodes is electrically charged when the first electrode is coupled to the fixed voltage source; and current is discharged from the electrical double layer when the first electrode is de-coupled from the fixed voltage source.

In certain embodiments the fixed voltage source, the first and second electrodes, and the switch are contained in an implantable device. In some embodiments the current discharged from the electrical double layer when the first electrode is de-coupled from the fixed voltage source stimulates the tissue. In particular embodiments the fixed voltage source has a potential of less than 5.0 volts. In specific embodiments the fixed voltage source has a potential of less than 3.0 volts. In certain embodiments the fixed voltage source has a potential of approximately 1.0 volts. In particular embodiments the first voltage potential is approximately 0 volts. In some embodiments the switch is configured to alternately couple the first electrode to the fixed voltage source for less than 100 µs and to de-couple the first electrode from the fixed voltage source for less than 100 µs. In specific embodiments the switch is configured to alternately couple the first electrode to the fixed voltage source for approximately 50 µs and to de-couple the first electrode from the fixed voltage source for approximately 50 µs. Certain embodiments further comprise a direct current (DC) blocking capacitor in series with the first electrode and the second electrode. Some embodiments further comprise a current sense resistor in series with the first electrode and the second electrode. In particular embodiments the switch is controlled via a microcontroller. In specific embodiments the switch is controlled by a resistor capacitor (RC) timer. In certain embodiments the resistor capacitor (RC) timer comprises a first resistor, a second resistor, a capacitor and a Schmitt trigger. In some embodiments the switch is coupled to the second electrode; and the switch is configured to alternately couple and de-couple the second electrode to the fixed voltage source.

Exemplary embodiments include a method of stimulating tissue, the method comprising: applying a first voltage potential to a first electrode and a second electrode, wherein the first electrode and the second electrode are proximal to the tissue; coupling the first electrode to a fixed voltage source to apply a second voltage potential to the first electrode; and de-coupling the first electrode from the fixed voltage source to apply the first voltage potential to the first electrode. In certain embodiments an electrical double layer between the tissue and the first and second electrodes is charged with an electrical current when the first electrode is coupled to the fixed voltage source; the electrical current is discharged from the electrical double layer when the first electrode is de-coupled from the fixed voltage source; and the tissue is stimulated via the electrical current.

Particular embodiments further comprise implanting the fixed voltage source and the first and second electrodes in the tissue in an implantable device. In some embodiments the fixed voltage source has a potential of less than 5.0, or 3.0 or 1.0 volts. In specific embodiments the first voltage potential is approximately 0 volts. In particular embodiments the first electrode is alternately coupled to the fixed voltage source for less than 100 µs and de-coupled to the fixed voltage source for less than 100 µs.

In certain embodiments the first electrode is alternately coupled to the fixed voltage source for approximately 50 µs and is de-coupled to the fixed voltage source for approximately 50 µs. In particular embodiments the electrical current passes through a direct current (DC) blocking capacitor in series with the first electrode and the second electrode. Specific embodiments further comprise monitoring the electrical current with a current sense resistor in series with the first electrode and the second electrode. In some embodiments the first electrode is coupled and de-coupled to the fixed voltage source by a switch controlled by a microcontroller. In certain embodiments the first electrode is coupled and de-coupled to the fixed voltage source by a switch controlled by a resistor capacitor (RC) timer. In some embodiments the resistor capacitor (RC) timer comprises a first resistor, a second resistor, a capacitor and a Schmitt trigger.

Particular embodiments further comprise: coupling the second electrode to the fixed voltage source to apply the second voltage potential to the second electrode; and de-coupling the second electrode from the fixed voltage source to apply the first voltage potential to the second electrode.

Exemplary embodiments include a system for nerve stimulation, the system comprising: a transceiver comprising: an electrical signal generator; and a transmission coil coupled to the electrical signal generator, where the transceiver is configured to transmit an alternating magnetic field from the transmission coil. Certain embodiments include an implantable device comprising: a receiving coil configured to receive the alternating magnetic field transmitted from the transmission coil and to induce an alternating current voltage; a rectifier coupled to the receiving coil and configured to rectify the alternating current voltage to direct current voltage; and a resistor capacitor (RC) timer coupled to the rectifier and configured to control a pulse duration and frequency applied to a plurality of stimulating electrodes. In particular embodiments the RC timer comprises a first resistor, a second resistor, and a capacitor and a Schmitt trigger. Some embodiments further comprise a linear regulator coupled to the rectifier and configured to regulate the amplitude of the direct current voltage.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
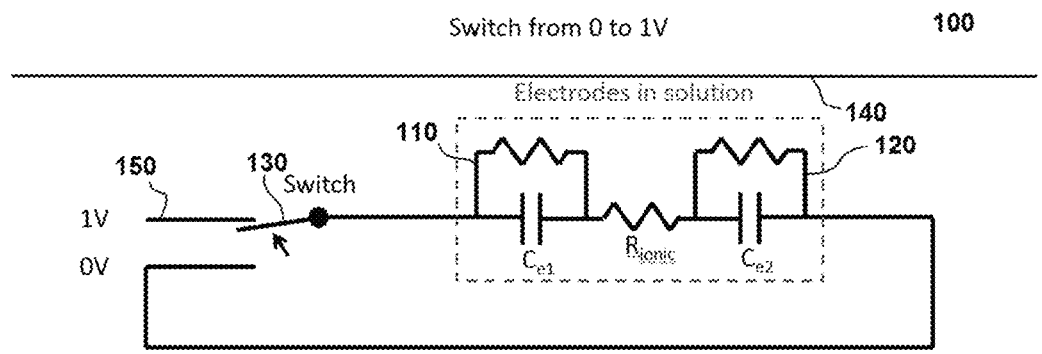
FIG. 1 illustrates a schematic of a tissue stimulation system according to exemplary embodiments of the present disclosure.

Referring now to FIG. 1, a nerve stimulation system 100 comprises first electrode 110 and second electrode 120. During operation, electrodes 110 and 120 begin at the same potential (zero volts in the embodiment shown), and one electrode is then switched via a switch 130 to a different potential (e.g., 1V) from a fixed voltage source 150. As used herein, the term "fixed voltage source" includes a voltage source that provides a relatively constant voltage level.

After the voltage switch is made to one electrode, current begins to flow from the electrode through tissue 140 proximal to electrodes 110 and 120. The current decreases exponentially with time due to the charging of the electrode double layer capacitance between the charged electrode and tissue 140. Once the electrode double layer capacitance has been charged, electrodes 110 and 120 are switched back to the same potential. Current is then discharged out of electrodes 110 and 120, decreasing exponentially over time.

Accordingly, exemplary embodiments utilize voltage controlled stimulation that operates by varying the voltage applied to electrodes 110 and 120. Unlike typical voltage controlled stimulation systems and methods, however, exemplary embodiments switch electrode 110 to fixed voltage source 150, rather than utilizing an electrode that is continuously connected to a variable voltage source.

In particular embodiments, switch 130 is configured to alternately couple first electrode 110 to fixed voltage source 150 for less than 100 µs (e.g. approximately 50 µs) and then to de-couple first electrode 110 from fixed voltage source 150 for less than 100 µs (e.g. approximately 50 µs). This process can be repeated so that tissue 140 is stimulated via the electrical current that is charged and discharged to and from the electrical double layer between tissue 140 and first and second electrodes 110 and 120.

Certain embodiments may also comprises a direct current (DC) blocking capacitor (not shown in FIG. 1) in series with first electrode 110 and second electrode 120. The inclusion of a DC blocking capacitor can restrict potentially harmful direct current from flowing through tissue 140. Particular embodiments may also include a sense resistor (not shown in FIG. 1) in series with first electrode 110 and second electrode 120. The sense resistor can be used to monitor the electrical current that stimulates tissue 140.

In certain embodiments, both electrodes 110 and 120 can be alternately coupled to fixed voltage source 150. This can provide for symmetrical charging and discharging of electrodes 110 and 120 so that the net charge on the electrodes is minimized over time.

In exemplary embodiments, switch 130 can be controlled via a number of different components. For example, switch 130 can be controlled via a microcontroller to alternately couple first electrode 110 (and in some embodiments, second electrode 120) to fixed voltage source 150. In other embodiments, switch 130 can be controlled by a resistor capacitor (RC) timer (not shown in FIG. 1). In specific embodiments, an RC timer can comprise a pair of resistors, a capacitor and a Schmitt trigger.

Figure 2:
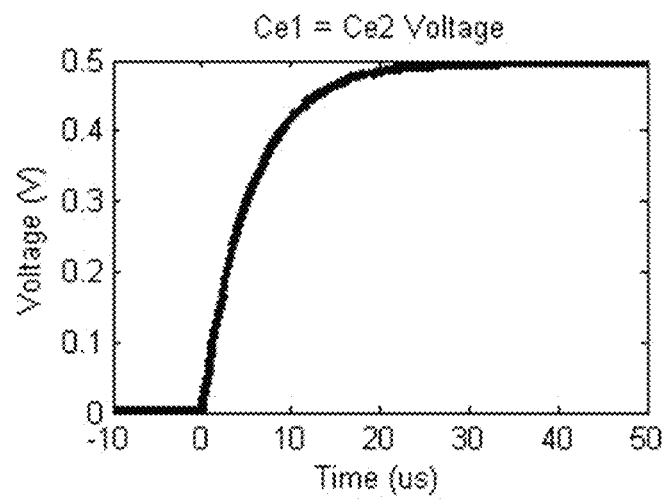
FIG. 2 illustrates a graph of voltage produced by the embodiment of FIG. 1 during operation.
Figure 3:
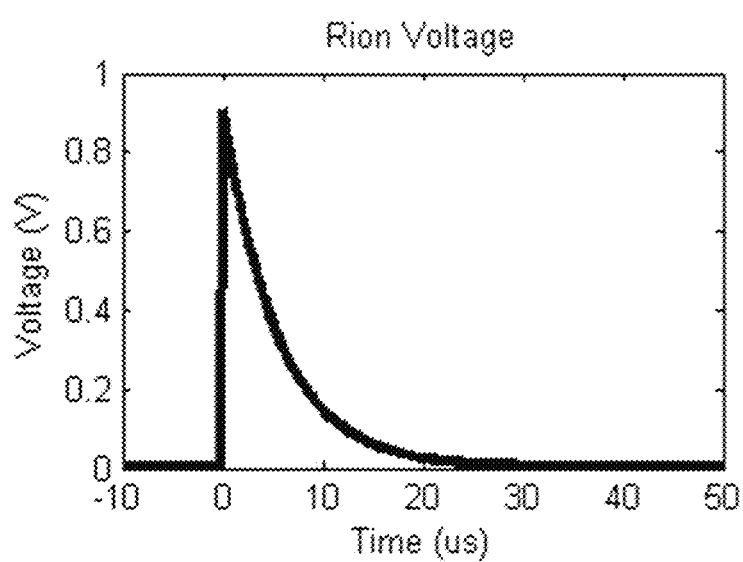
FIG. 3 illustrates a graph of voltage produced by the embodiment of FIG. 1 during operation.

Examples of voltage over time for $C_{e1}$, $C_{e2}$ and $R_{ionic}$ produced by system 100 are shown in FIGS. 2 and 3. It is understood that the elements labeled $C_{e1}$ and $C_{e2}$ and are not separate electronic components (e.g. capacitors), but instead represent the capacitance formed between tissue 140 and the conductive surface of electrodes 110 and 120. Similarly, the element $R_{ionic}$ is not a separate resistor, but instead represents the resistance of the fluid in tissue 140.

FIG. 2 illustrates the voltage between each of electrodes 110 and 120 and tissue 140 (e.g. from the capacitance between the surface of the electrodes 110 and 120 and fluid in tissue 140). In FIG. 2, first electrode 110 is coupled to fixed voltage source 150 via switch 130 at time 0. First electrode 110 remains coupled to fixed voltage source for 50 µs in this embodiment, but it is understood that in other embodiments, first electrode 110 may remain coupled to fixed voltage source for different lengths of time. FIG. 3 illustrates an example of the voltage over time tissue 140 based on the ionic resistance of fluid in tissue 140.

Figure 4:
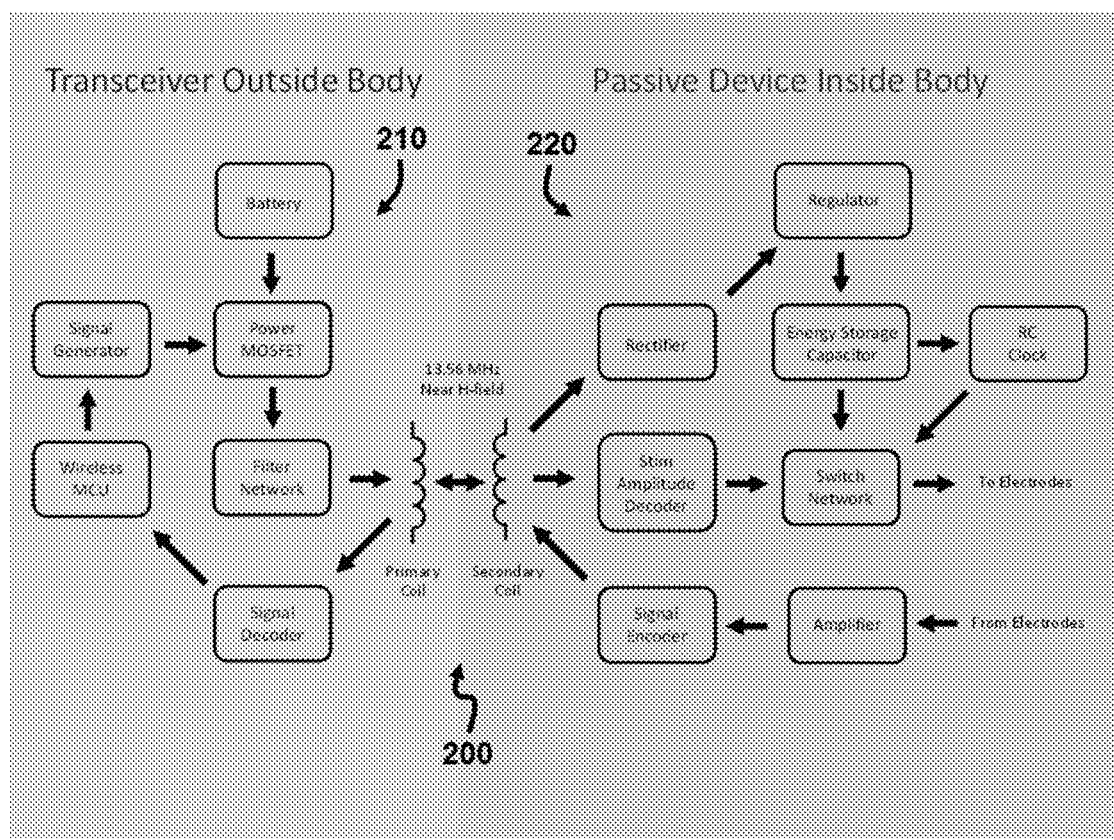
FIG. 4 illustrates a schematic of a tissue stimulation system comprising a transceiver and a passive implant.
Figure 5:
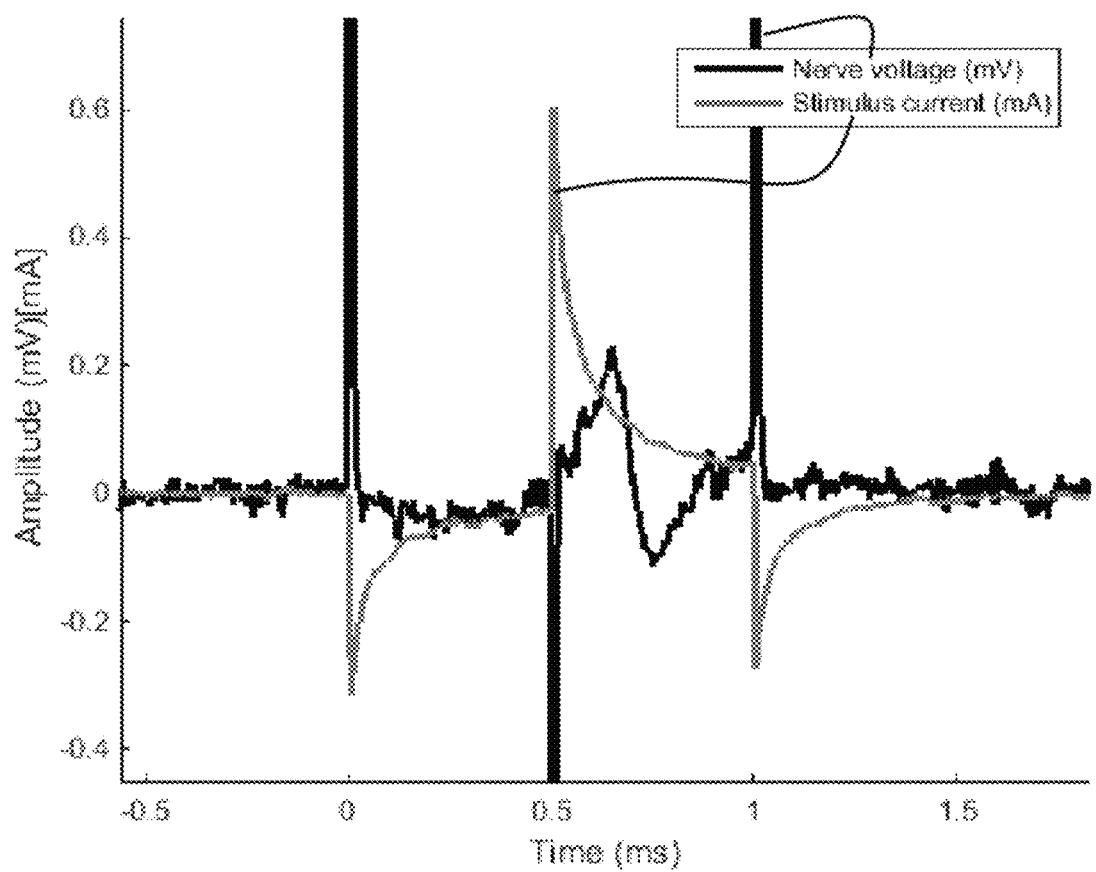
FIG. 5 illustrates a graph of nerve voltage and stimulus current versus time is shown for the system of FIG. 4.
Figure 6:
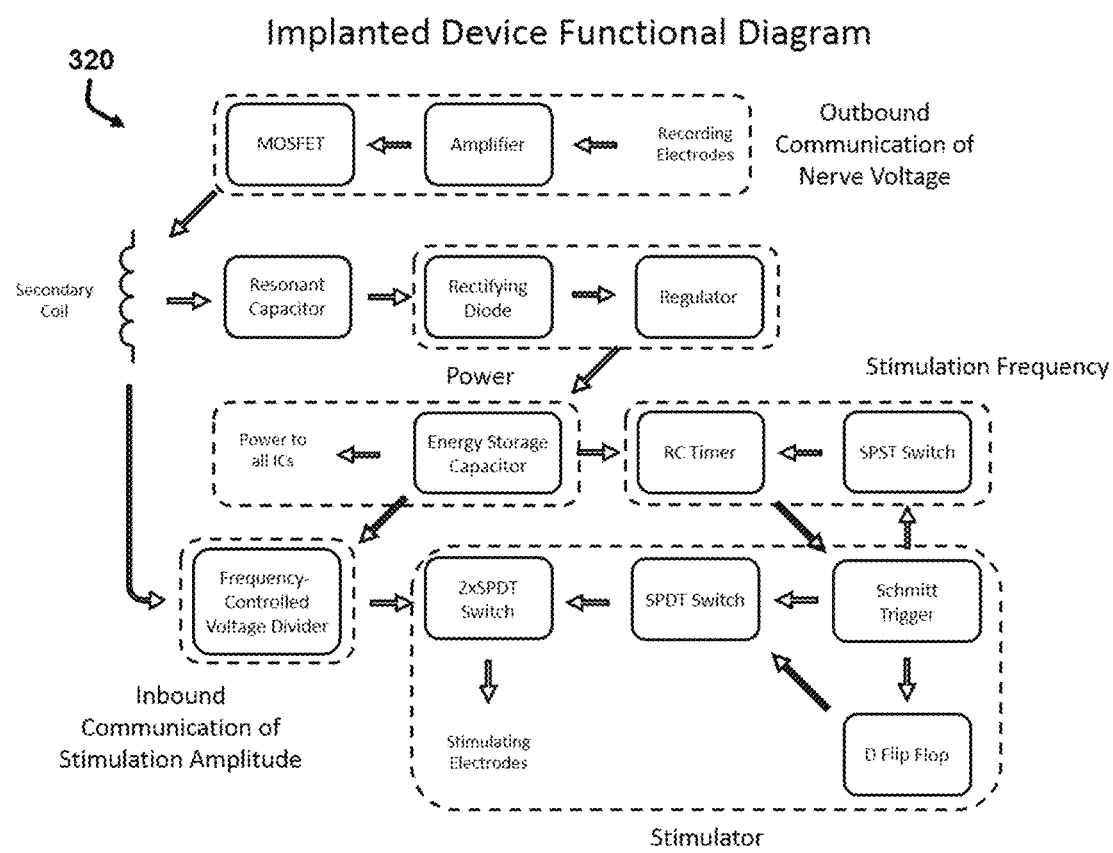
FIG. 6 illustrates a functional block diagram of a passive implant with specific electronic components.

Referring now to FIGS. 4-6 exemplary embodiments are directed to a low-power, low cost approach to an implanted device/system for wireless stimulation and recording using passive components (as opposed to wireless systems that employ complex circuitry for power generation, transmission, rectification, and modulation found in typical systems). In exemplary embodiments, the electrodes and associated components are configured as an implantable device with a stimulation circuit comprising a voltage source and a signal that controls the switch. In specific embodiments, additional components can be added to improve device robustness or to gain finer control over stimulation parameters.

Referring specifically now to FIG. 4, an overview schematic of a tissue stimulation system 200 comprises a transceiver 210 and a passive implant 220. Implant 220 is powered on by an external receiver (containing coils generating magnetic field) and starts stimulating the tissue through the implanted electrodes. Referring now to FIG. 5, a graph of nerve voltage and stimulus current versus time is shown for the device according to FIG. 4.

Referring now to FIG. 6, a functional block diagram of a passive implant 320 is shown with specific electronic components. In particular embodiments, a voltage source can be obtained by rectifying secondary (e.g. receiving) coil voltage with a diode. In some embodiments, a regulator can be used to limit this voltage to a specified value, and in specific embodiments, the regulators can be Zener diodes or low dropout (LDO) style linear regulators. In certain embodiments, a resistor capacitor (RC) timer can be used to control the switched electrode stimulator circuit, and in particular embodiments, the RC timer can be constructed using two resistors, a capacitor, and a Schmitt trigger. The RC timer can generate regular digital pulses that control the switches, with the pulse duration and frequency set by the values of resistors.

In order to switch both electrodes alternatingly, an additional switch and data (D) flip-flop can be used to allow for symmetric charging/discharging of electrodes and prevent net charge from accumulating over time. To control stimulation amplitude, a frequency controlled voltage (FCV) circuit can be used in certain embodiments. This circuit creates a voltage divider using a resistor and an inductor and capacitor (LC) tank. Small adjustments to the frequency of the incoming RF field cause the impedance of the LC tank to change, thereby changing the voltage divider ratio. Since the quality factor of the LC tank is higher than the quality factor of the secondary coil, small adjustments to the frequency have minimal effect on incoming power.

During operation, signals of interest can be communicated out of the body by modulating the secondary coil. Nerve voltage can be amplified and used to directly control a metal-oxide-semiconductor field-effect transistor (MOSFET), which modulates the secondary coil. The stimulation current can be sensed and communicated out using the same method.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

References

[1] R. R. Harrison, P. T. Watkins, R. J. Kier, R. O. Lovejoy, D. J. Black, B. Greger, and F. Solzbacher, "A low-power integrated circuit for a wireless 100-electrode neural recording system," *IEEE J. Solid-State Circuits*, vol. 42, no. 1, pp. 123-133, 2007.

[2] S. B. Lee, H. M. Lee, M. Kiani, U. M. Jow, and M. Ghovanloo, "An inductively powered scalable 32-channel wireless neural recording system-on-a-chip for neuroscience applications," *IEEE Trans. Biomed. Circuits Syst.*, vol. 4, no. 6, pp. 360-371, 2010.

[3] A. M. Sodagar, K. D. Wise, and K. Najafi, "A wireless implantable microsystem for multichannel neural recording," *IEEE Trans. Microw. Theory Tech.*, vol. 57, no. 10, pp. 2565-2573, 2009.

[4] Systems and Methods for multichannel wireless implantable neural recording, GTech, US Patent 2010/0106041 A1

[5] Implantable Wireless Neural Device, Brown University, US Patent 2014/0094674 A1.

[6] Grooved electrode and wireless microtransponder system, Microtransponder, U.S. Pat. No. 7,603,0771 B2

[7] Microtransponder, "Implantable Transponder Systems and Methods," U.S. Pat. No. 8,457,757 B2, vol. 2, no. 12, 2013.
  Batterless, passive implant, wirless stimulation of multiple implants for perpherial nerves. Can be set to operate in different modes.

[8] W. M. Rosellini, P. B. Yoo, N. Engineer, S. Armstrong, R. L. Weiner, C. Burress, and L. Cauller, "A Voltage-Controlled Capacitive Discharge Method for Electrical Activation of Peripheral Nerves," *Neuromodulation Technol. Neural Interface*, vol. 14, no. 6, pp. 493-500, 2011.

[9] J. Vidal and M. Ghovanloo, "Towards a Switched-Capacitor based Stimulator for efficient deep-brain stimulation," *Conf. Proc. . . . Annu. Int. Conf. IEEE Eng. Med. Biol. Soc. IEEE Eng. Med. Biol. Soc. Annu. Conf.*, vol. 2010, pp. 2927-30, 2010.

[10] M. Catrysse, B. Hermans, and R. Puers, "An inductive power system with integrated bi-directional data-transmission," *Sensors Actuators, A Phys.*, vol. 115, pp. 221-229, 2004.

[11] H. Chun, T. Lehmann, and Y. Yang, "Implantable stimulator for bipolar stimulation without charge balancing circuits," in *Biomedical Circuits and Systems Conference (BioCAS)*, 2010 IEEE, 2010, pp. 202-205.

The invention claimed is:

1. A system for stimulating tissue, the system comprising:
  a fixed voltage source;
  a first electrode;
  a second electrode; and
  a switch coupled to the first electrode, wherein:
    the first electrode and the second electrode are initially at a first voltage potential;
    the fixed voltage source is at a second voltage potential; and
    the switch is configured to alternately couple and de-couple the first electrode to the fixed voltage source, wherein:
      an electrical double layer between the tissue and the first and second electrodes is electrically charged when the first electrode is coupled to the fixed voltage source;
      current is discharged from the electrical double layer when the first electrode is de-coupled from the fixed voltage source; and
      the switch is controlled by a resistor capacitor (RC) timer.

2. The system of claim 1 wherein the fixed voltage source, the first and second electrodes, and the switch are contained in an implantable device.

3. The system of claim 1 wherein the current discharged from the electrical double layer when the first electrode is de-coupled from the fixed voltage source stimulates the tissue.

4. The system of claim 1 wherein the fixed voltage source has a potential of less than 3.0 volts.

5. The system of claim 1 wherein the first voltage potential is approximately 0 volts.

6. The system of claim 1 further comprising a direct current (DC) blocking capacitor in series with the first electrode and the second electrode.

7. The system of claim 1 further comprising a current sense resistor in series with the first electrode and the second electrode.

8. The system of claim 1 wherein the switch is controlled via a microcontroller.

9. The system of claim 1 wherein the resistor capacitor (RC) timer comprises a first resistor, a second resistor, a capacitor and a Schmitt trigger.

10. The system of claim 1 wherein:
  the switch is coupled to the second electrode; and
  the switch is configured to alternately couple and de-couple the second electrode to the fixed voltage source.

11. A system for stimulating tissue, the system comprising:
  a fixed voltage source;
  a first electrode;
  a second electrode; and
  a switch coupled to the first electrode, wherein:
    the first electrode and the second electrode are initially at a first voltage potential;
    the fixed voltage source is at a second voltage potential; and the switch is configured to alternately couple and de-couple the first electrode to the fixed voltage source, wherein:
an electrical double layer between the tissue and the first and second electrodes is electrically charged when the first electrode is coupled to the fixed voltage source; and
current is discharged from the electrical double layer when the first electrode is de-coupled from the fixed voltage source, wherein the switch is configured to alternately couple the first electrode to the fixed voltage source for approximately 50 µs and to de-couple the first electrode from the fixed voltage source for approximately 50 µs.

12. A method of stimulating tissue, the method comprising:
applying a first voltage potential to a first electrode and a second electrode, wherein the first electrode and the second electrode are proximal to the tissue;
coupling the first electrode to a fixed voltage source to apply a second voltage potential to the first electrode; and
de-coupling the first electrode from the fixed voltage source to apply the first voltage potential to the first electrode, wherein:
an electrical double layer between the tissue and the first and second electrodes is charged with an electrical current when the first electrode is coupled to the fixed voltage source;
the electrical current is discharged from the electrical double layer when the first electrode is de-coupled from the fixed voltage source;
the tissue is stimulated via the electrical current; and
further comprising monitoring the electrical current with a current sense resistor in series with the first electrode and the second electrode.

13. The method of claim 12 further comprising implanting the fixed voltage source and the first and second electrodes in the tissue in an implantable device.

14. The method of claim 12 wherein the electrical current passes through a direct current (DC) blocking capacitor in series with the first electrode and the second electrode.

15. The method of claim 12 further comprising:
coupling the second electrode to the fixed voltage source to apply the second voltage potential to the second electrode; and
de-coupling the second electrode from the fixed voltage source to apply the first voltage potential to the second electrode.

16. A system for stimulating tissue, the system comprising:
a fixed voltage source;
a first electrode;
a second electrode; and
a switch coupled to the first electrode, wherein:
the first electrode and the second electrode are initially at a first voltage potential;
the fixed voltage source is at a second voltage potential; and
the switch is configured to alternately couple and de-couple the first electrode to the fixed voltage source, wherein:
an electrical double layer between the tissue and the first and second electrodes is electrically charged when the first electrode is coupled to the fixed voltage source; and
current is discharged from the electrical double layer when the first electrode is de-coupled from the fixed voltage source, wherein:
the fixed voltage source, the first electrode, the second electrode and the switch are contained in an implantable device;
the system further comprises a transceiver comprising:
an electrical signal generator; and
a transmission coil coupled to the electrical signal generator, wherein the transceiver is configured to transmit an alternating magnetic field from the transmission coil; and
the implantable device further comprises:
a receiving coil configured to receive the alternating magnetic field transmitted from the transmission coil and to induce an alternating current voltage;
a rectifier coupled to the receiving coil and configured to rectify the alternating current voltage to direct current voltage; and
a resistor capacitor (RC) timer coupled to the rectifier and configured to control a pulse duration and frequency applied to the first electrode and the second electrode.

17. The system of claim 16 wherein the RC timer comprises a first resistor, a second resistor, a capacitor and a Schmitt trigger; and, wherein the system further comprises:
a rectifier; and
a linear regulator coupled to the rectifier configured to regulate the amplitude of the direct current voltage.

* * * * *